United States Patent

Stahle et al.

[11] 3,937,717
[45] Feb. 10, 1976

[54] 2-PHENYLAMINO-IMIDAZOLINES-(2)

[75] Inventors: Helmut Stahle; Herbert Koppe; Werner Kummer; Klaus Stockhaus, all of Ingelheim am Rhein, Germany

[73] Assignee: Boehringer Ingelheim GmbH, Ingelheim am Rhein, Germany

[22] Filed: Feb. 11, 1974

[21] Appl. No.: 441,451

[30] Foreign Application Priority Data
Feb. 23, 1973  Germany............................ 2308883

[52] U.S. Cl..... 260/309.6; 260/329 AM; 260/332.5; 260/500.5 R; 424/273
[51] Int. Cl.²......................................... C07D 49/34
[58] Field of Search .................................. 260/309.6

[56] References Cited
UNITED STATES PATENTS

| | | | |
|---|---|---|---|
| 3,147,270 | 9/1964 | Anderson.......................... | 260/309.6 |
| 3,236,857 | 2/1966 | Zeile et al......................... | 260/309.6 |
| 3,746,724 | 7/1973 | Werner et al.................. | 260/309.6 X |
| 3,758,476 | 9/1973 | Rippel et al. ................ | 260/309.6 X |

OTHER PUBLICATIONS
C.A. 75 – 140850a.
C.A. 74 – 100054s.

*Primary Examiner*—Ethel G. Love
*Attorney, Agent, or Firm*—Hammond & Littell

[57] ABSTRACT
2-Phenylamino-imidazolines-(2) of the formula

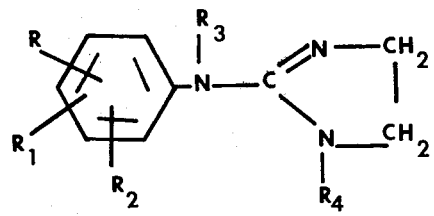

wherein R, $R_1$ and $R_2$ are individually selected from the group consisting of hydrogen, fluorine, chlorine, bromine, methyl, ethyl, methoxy, trifluoromethyl and cyano and one of $R_3$ and $R_4$ being hydrogen while the other is

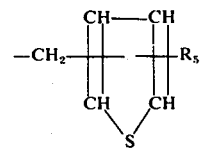

and $R_5$ is selected from the group consisting of hydrogen, methyl and ethyl and their non-toxic, pharmaceutically acceptable acid addition salts which have analgesic and blood pressure reducing properties and their preparation.

5 Claims, No Drawings

2-PHENYLAMINO-IMIDAZOLINES-(2)

OBJECTS OF THE INVENTION

It is an object of the invention to provide the novel 2-phenylamino-imidazolines-(2) of formula I and their nontoxic, pharmaceutically acceptable acid addition salts.

It is another object of the invention to provide a novel process for the preparation of the compounds of formula I.

It is a further object of the invention to provide novel analgesic compositions and it is an additional object of the invention to provide a novel method of relieving pain in warm-blooded animals.

These and other objects and avantages of the invention will become obvious from the following detailed description.

THE INVENTION

The novel products of the invention are selected from the group consisting of 2-phenylamino-imidazolines-(2) of the formula

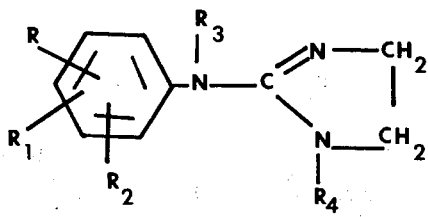

wherein R, $R_1$ and $R_2$ are individually selected from the group consisting of hydrogen, fluorine, chlorine, bromine, methyl, ethyl, methoxy, trifluoromethyl and cyano and one of $R_3$ and $R_4$ being hydrogen while the other is

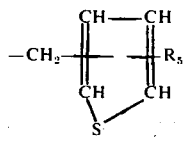

and $R_5$ is selected from the group consisting of hydrogen, methyl and ethyl and their non-toxic, pharmaceutically acceptable acid addition salts.

Examples of suitable acids for the non-toxic, pharmaceutically acid addition salts are mineral acids such as hydrochloric acid, hydrobromic acid, hydriodic acid, hydrofluoric acid, sulfuric acid, phosphoric acid and nitric acid or organic acids such as acetic acid, propionic acid, butyric acid, valeric acid, caproic acid, caprinic acid, oxalic acid, malonic acid, succinic acid, glutaric acid, maleic acid, fumaric acid, lactic acid, tartaric acid, citric acid, malic acid, gluconic acid, benzoic acid, p-hydroxybenzoic acid, phthalic acid, cinnamic acid, salicylic acid, ascorbic acid, 8-chlorotheophylline and methanesulfonic acid.

Examples of suitable compounds of formula I are:

2-[N-(thienyl-(2)-methyl)-N-(2,6-dichlorophenyl-amino]-imidazoline-(2)
2-[N-(thienyl-(2)-methyl)-N-(2-chloro-6-methyl-phenyl)-amino]-imidazoline-(2)
2-[N-(thienyl-(2)-methyl)-N-(2-chloro-4-methyl-phenyl)-amino]-imidazoline-(2)
2-[N-(thienyl-(2)-methyl)-N-(2-methyl-5-fluoro-phenyl)-amino]-imidazoline-(2)
2-[N-(thienyl-(3)-methyl)-N-(2,6-dichlorophenyl)-amino]-imidazoline-(2)
2-[N-(thienyl-(3)-methyl)-N-(4-methoxyphenyl)-amino]-imidazoline-(2)
2-[N-(thienyl-(3)-methyl)-N-(2,6-dichloro-4-bromo-phenyl)-amino]-imidazoline-(2)
2-[N-(thienyl-(2)-methyl)-N-(2,6-dichloro-4-bromo-phenyl)-amino]-imidazoline-(2)
2-[N-(thienyl-(2)-methyl)-N-(2-trifluoromethyl-phenyl)-amino]-imidazoline-(2)
2-[N-(thienyl-(2)-methyl)-N-(2,6-diethylphenyl)-amino]-imidazoline-(2)
2-[N-(thienyl-(3)-methyl)-N-(2,6-diethylphenyl)-amino]-imidazoline-(2)
2-[N-(thienyl-(3)-methyl)-N(2,6-dimethylphenyl)-amino]-imidazoline-(2)
2-[N-(thienyl-(3)-methyl)-N-(2,6-dimethylphenyl)-amino]-imidazoline-(2)
2-[N-(thienyl-(2)-methyl)-N-(2-chloro-6-ethyl-phenyl)-amino]-imidazoline-(2)
2-[N-(thienyl-(3)-methyl)-N-(2-chloro-6-ethyl-phenyl)-amino]-imidazoline-(2)
2-[N-(thienyl-(3)-methyl)-N-(2-chloro-6-methyl-phenyl)-amino]-imidazoline-(2)
2-[N-(thienyl-(3)-methyl)-N-(2-chloro-4-methyl-phenyl)-amino]-imidazoline-(2)
2-[N-(thienyl-(2)-methyl)-N-(phenyl)-amino]-imidazoline-(2)
2-[N-(thienyl-(2)-methyl)-N-(2-chloro-3-methyl-phenyl)-amino]-imidazoline-(2)
2-[N-(thienyl-(3)-methyl)-N-(2-chloro-3-methyl-phenyl)-amino]-imidazoline-(2)
2-[N-(thienyl-(2)-methyl)-N-(2,4-dichlorophenyl)-amino]-imidazoline-(2)
2-[N-(thienyl-(3)-methyl)-N-(2,4-dichlorophenyl)-amino]-imidazoline-(2)
2-[N-(thienyl-(2)-methyl)-N-(2,3-dichlorophenyl)-amino]-imidazoline-(2)
2-[N-(thienyl-(3)-methyl)-N-(2,3-dichlorophenyl)-amino]-imidazoline-(2)
2-[N-(thienyl-(2)-methyl)-N-(2,5-dichlorophenyl)-amino]-imidazoline-(2)
2-[N-(thienyl-(3)-methyl)-N-(2,5-dichlorophenyl)-amino]-imidazoline-(2)
2-[N-(thienyl-(2)-methyl)-N-(2,6-dibromophenyl)-amino]-imidazoline-(2)
2-[N-(thienyl-(3) -methyl)-N-(2,6-dibromophenyl)-amino]-imidazoline-(2)
2-[N-(thienyl-(2)-methyl)-N-(2,6-difluorophenyl)-amino]-imidazoline-(2)
2-[N-(thienyl-(3)-methyl)-N-(2,6-difluorophenyl)-amino]-imidazoline-(2)
2-[N-(3-methylthienyl-(2)-methyl)-N-(2,6-dichloro-phenyl)-amino]-imidazoline-(2)
2-[N-(2-methylthienyl-(3)-methyl)-N-(2,6-dichloro-phenyl)-amino]-imidazoline-(2)
2-[N-(3-methylthienyl-(4)-methyl)-N-(2,6-dichloro-phenyl)-amino]-imidazoline-(2)
2-[N-(2-methylthienyl-(4)-methyl)-N-(2,6-dichloro-phenyl)-amino]-imidazoline-(2)
2-[N-(2-methylthienyl-(5)-methyl)-N-(2,6-dichloro-phenyl)-amino]-imidazoline-(2)
2-[N-(4-methylthienyl-(2)-methyl)-N-(2,6-dichloro-phenyl)-amino]-imidazoline-(2)
2-[N-(3-ethylthienyl-(2)-methyl)-N-(2,6-dichlorophe-nyl-amino]-imidazoline-(2)

2-[N-(2-ethylthienyl-(3)-methyl)-N-(2,6-dichlorophenyl)-amino]-imidazoline-(2)
2-[N-(3-ethylthienyl-(4)-methyl)-N-(2,6-dichlorophenyl)-amino]-imidazoline-(2)
2-[N-(2-ethylthienyl-(4)-methyl)-N-(2,6-dichlorophenyl)-amino]-imidazoline-(2)
2-[N-(2-ethylthienyl-(5)-methyl)-N-(2,6-dichlorophenyl)-amino]-imidazoline-(2)
2-[N-(4-ethylthienyl-(2)-methyl)-N-(2,6-dichlorophenyl)-amino]-imidazoline-(2)
2-[N-(3-methylthienyl-(2)-methyl)-N-(2-chloro-3-methylphenyl)-amino]-imidazoline-(2)
2-[N-(thienyl-(2)-methyl)-N-(2,4-difluorophenyl)-amino]-imidazoline-(2)
2-[N-(3-methylthienyl-(2)-methyl)-N-(2,4-dichlorophenyl)-amino]-imidazoline-(2)
2-[N-(2-methylthienyl-(3)-methyl)-N-(2,3-dichlorophenyl)-amino]-imidazoline-(2)
2-[N-(3-methylthienyl-(4)-methyl)-N-(2-chloro-4-methylphenyl)-amino]-imidazoline-(2)
2-[N-(2-methylthienyl-(4)-methyl)-N-(4-chloro-2-methylphenyl)-amino]-imidazoline-(2)
2-[N-(2-methylthienyl-(5)-methyl)-N-(2-methyl-5-fluoromethyl)-amino]-imidazoline-(2)
2-[N-(4-methylthienyl-(2)-methyl)-N-(2-chloro-6-methylphenyl)-amino]-imidazoline-(2)
2-[N-(3-ethylthienyl-(2)-methyl)-N-(2-methyl-5-fluorophenyl)-amino]-imidazoline-(2)
2-[N-(2-ethylthienyl-(3)-methyl)-N-(2-chloro-4-methylphenyl)-amino]-imidazoline-(2)
2-[N-(3-ethylthienyl-(4)-methyl)-N-(2,6-diethylphenyl)-amino]-imidazoline-(2)
2-[N-(2-methylthienyl-(5)-methyl)-N-(2-methyl-5-fluorophenyl)-amino]-imidazoline-(2)
2-[N-(4-methylthienyl-(2)-methyl)-N-(2-chloro-6-methylphenyl)-amino]-imidazoline-(2)
2-[N-(3-ethylthienyl-(2)-methyl)-N-(2-methyl-5-fluorophenyl)-amino]-imidazoline-(2)
2-[N-(2-ethylthienyl-(3)-methyl)-N-(2-chloro-4-methylphenyl)-amino]-imidazoline-(2)
2-[N-(3-ethylthienyl-(4)-methyl)-N-(2,6-diethylphenyl)-amino]-imidazoline-(2)
2-[N-(2-ethylthienyl-(4)-methyl)-N-(2,5-dichlorophenyl)-amino]-imidazoline-(2)
2-[N-(2-ethylthienyl-(5)-methyl)-N-(2,6-dibromophenyl)-amino]-imidazoline-(2)
2-[N-(2-ethylthienyl-(2)-methyl)-N-(2,6-dichloro-4-bromophenyl)-amino]-imidazoline-(2)
1-(thienyl-(2)-methyl)-2-(2,6-dichlorophenylamino)-2-imidazoline
1-(thienyl-(3)-methyl)-2-(2,6-dichlorophenylamino)-2-imidazoline
1-(2-methylthienyl-(3)-methyl)-2-(2,6-dichlorophenylamino)-2-imidazoline
1-(3-methylthienyl-(2)-methyl)-2-(2,6-dichlorophenylamino)-2-imidazoline
1-(3-methylthienyl-(4)-methyl)-2-(2,6-dichlorophenylamino)-2-imidazoline
1-(2-methylthienyl-(4)-methyl)-2-(2,6-dichlorophenylamino)-2-imidazoline
1-(2-methylthienyl-(5)-methyl)-2-(2,6-dichlorophenylamino)-2-imidazoline
1-(4-methylthienyl-(2)-methyl)-2-(2,6-dichlorophenylamino)-2-imidazoline
1-(2-methylthienyl-(3)-methyl)-2-(2-chloro-4-methylphenylamino)-2-imidazoline
1-(2-methylthienyl-(3)-methyl)-2-(2-chloro-3-methylphenylamino)-2-imidazoline
1-(2-methylthienyl-(3)-methyl)-2-(5-fluoro-2-methylphenylamino)-2-imidazoline
1-(2-methylthienyl-(3)-methyl)-2-(2,6-diethylphenylamino)-2-imidazoline
1-(3-methylthienyl-(2)-methyl)-2-(2,6-dimethylphenylamino)-2-imidazoline
1-(3-methylthienyl-(4)-methyl))-2-(2,6-diethylphenylamino)-2-imidazoline
1-(3-ethylthienyl-(2)-methyl)-2-(2,6-dichlorophenylamino)-2-imidazoline
1-(3-ethylthienyl-(2)-methyl)-2-(2,3-dichlorophenylamino))-2-imidazoline
1-(2-ethylthienyl-(3)-methyl)-2-(2,6-dichlorophenylamino)-2-imidazoline
1-(2-ethylthienyl-(3)-methyl)-2-(5-fluoro-2-methylphenylamino)-2-imidazoline
1-(2-ethylthienyl-(3)-methyl)-2-(2-chloro-4-methylphenylamino)-2-imidazoline
1-(2-ethylthienyl-(3)-methyl)-2-(2-chloro-3-methylphenylamino)-2-imidazoline
1-(3-ethylthienyl-(2)-methyl)-2-(2-methyl-3-bromophenylamino)-2-imidazoline The compounds of formula I may be produced by
a) reacting a 2-phenylamino-imidazoline-(2) of formula II

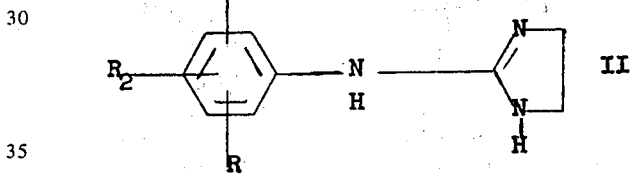

wherein R, $R_1$ and $R_2$ have the above meanings with a halide of the formula

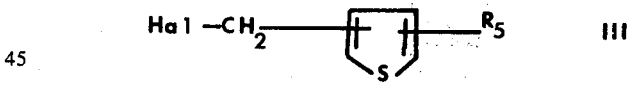

wherein Hal is chlorine, bromine or iodine and $R_5$ has the above meaning; or
b) by reacting a compound of the formula

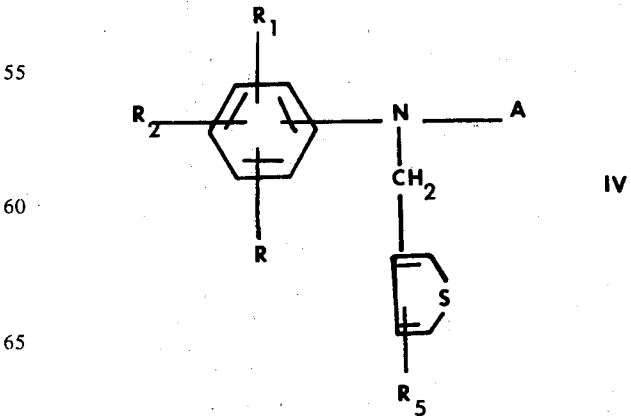

wherein R, $R_1$, $R_2$ and $R_5$ are defined as above and A is

and Y is alkoxy or alkylthio with up to 4 carbon atons or sulfhydryl or amino with ethylenediamine or the acid addition salts thereof; or

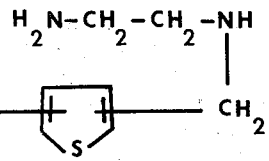            VII wherein $R_5$ is defined as above; or d) by reacting metal salts of 2-phenylamino-imidazolines-(2) of the formula c) by reacting compounds of the formula

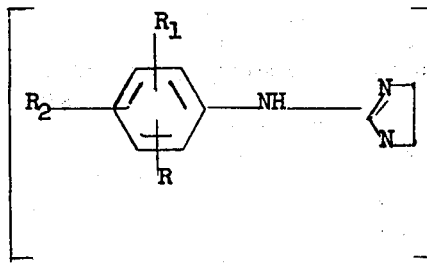            VIII wherein R, $R_1$ and $R_2$ have the above meanings and $Me^{(+)}$ is a metal cation, preferably an alkali metal cation, more preferably $Na^{(+)}$, with a halide of the formula

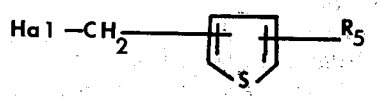            III

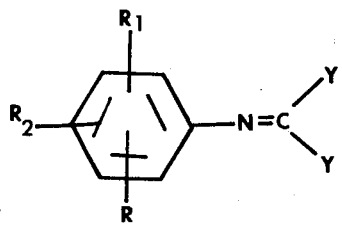            V wherein Hal and $R_5$ are defined as above.

When alkylating the 2-arylamino-imidazolines-(2) of formula II in accordance with process a), the substitution is effected exclusively at the bridge nitrogen atom. When reacting in accordance with processes b) and c), the constitution of the final compounds is established by the synthesis. While working in accordance with process d), the imidazoline derivatives substituted at the imidazoline nitrogen are preferably obtained. Also produced in low yields are the isomeric compounds substituted at the bridge nitrogen. In each case, the position of the substituent may be determined by the synethesis as well as by NMR-spectroscopy [compare Stahle et al., Liebigs Ann. Chem. 751, 159 ff (1971)].

wherein R, $R_1$ and $R_2$ are defined as above and X and Y, which may be identical to or different from each other, are halogen, preferably chlorine, sulfhydryl, an amino, alkoxy or alkylthio, or reacting compounds of the formula The reaction in accordance with process a) is appropriately effected by heating the reactants preferably in the presence of a polar or nonpolar organic solvent to temperatures of about 50 to 150°C. The specific reaction conditions depend to a high degree upon the reactivity of the reactants and it is recommended to use the halide in excess for alkylation and to effect the reaction in the presence of an acidbinding agent.

With process b), it is required to work at elevated temperature of about 60° to 180°C. Solvents are not necessary but it is useful to use the ethylenediamine or its acid addition salt which is a reactant in excess.

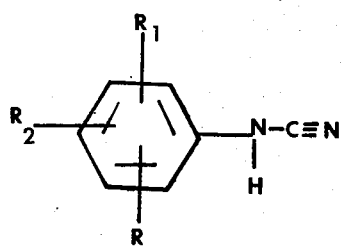            VI wherein R, $R_1$ and $R_2$ have the above meanings with diamines of the formula Reaction c) is effected at temperatures between 0° and 180°C depending upon the groups X and Y. Suitable solvents depending upon groups X and Y, may be polar or polar-aprotic ones. If one of X or Y is a halogen, it is recommended to use an acid-binding agent in the reaction. The reaction time depends on the reactivity of the components used and varies from several minutes to several hours.

Process d) is carried out best in a non-polar organic solvent, such as tetrahydrofuran, at elevated temperatures of up to 150°C. The reaction time is usually 1 to 2 hours.

Starting compounds of formula II have been described, for example, in Belgian Pat. Nos. 623,305, 687,656, 687,657 and 705,944. Starting compounds of formula III may be prepared by known process such as halo-methylation of thiphenes or reduction of thiophencarbonate with metal hydrides to hydroxymethyl-thiophenes and subsequent exchange of the hydroxy with halogens. Chloromethylthiophenes may be converted into corresponding bromo- or iodomethyl derivatives by reaction with alkali metal bromides or alkali metal iodides.

Compounds of formula IV may be prepared by reacting anilines with compounds of formula III and subsequent reaction of the secondary amines originating therefrom with cyanates or thiocyanates whereby ureas or thioureas are formed. Ureas and thioureas may then be converted further with alkylation agents into corresponding isouronium salts or isothiouronium salts. The said acid addition compounds may be reacted with bases to form the corresponding isoureas or isothioureas. By splitting off water from ureas or $H_2S$-splitting from thioureas with lead or mercury salts, cynamides are obtained to which ammonia may be added to form guanidines.

Starting compounds of formula V are disclosed, for example, in Belgian Pat. No. 705,944 while compounds of formula VI may be prepared by reacting anilines with halocyan or by splitting off hydrogen sulfide from corresponding phenylthioureas with lead or mercury salts. Compounds of formula VII may be prepared by reacting compounds of formula III with ethylenediamine. Compounds of formula II may be metallized by reaction with metal alkyls or metal hydrides under anhydrous conditions to form compounds of formula VIII.

The noval analgesic compositions of the invention are comprised of an effective amount of at least one compound of formula I or its non-toxic, pharmaceutically acceptable acid addition salts and a pharmaceutical carrier. The composition may be in the form of tablets, capsules, suppositories, solutions or powders and may contain other active ingredients. Because of their analgesic and blood pressure reducing properties, the compositions are useful for the treatment of various types of pain such as migrain headaches or for the treatment of high blood pressure.

The compositions can be prepared with known galenic excipients, carriers, disintegrating agents, lubricants or sustained release agents.

Tablets may be obtained by mixing the active ingredients with known excipients, for example, with inert diluents such as calcium carbonate, calcium phosphate or lactose; disintegrants such as corn starch or alginic acid; binders such as starch or gelatin; lubricants such as magnesium stearate or talc; and/or agents for sustained release such as carboxypolymethylene, carboxymethylcellulose, cellulose acetate phthalate or polyvinylacetate.

The tablets may also have several layers and coated tablets may be produced by coating cores prepared analogous to the tablets with agents commonly used for coating tablets such as polyvinylpyrrolidone, shellac, gum arabic, talcum, titanium dioxide or sugar. To obtain sustained release or to avoid incompatibilities, the core may also consist of several layers. The tablet-coat is preferably made of several layers to obtain sustained release whereby the auxiliaries mentioned above for the tablets may be used.

For production of soft gelatin capsules or of similar sealed capsules, the active substance may be admixed with a plant oil. Hard gelatin capsules may contain granulates of the active substance with solid carriers in powder form such as lactose, saccharose, sorbitol, mannitol, starch such as potoato starch, corn starch or amylopetin, cellulose derivatives or gelatin.

Syrups of the active ingredients of the invention or active ingredient combinations may also contain a sweetner such as saccharin, cyclamate, glycerin or sugar, as well as an agent improving the taste such as flavors like vanillin or orange extract. They may also contain suspension auxiliaries or thickeners, such as sodium carboxymethylcellulose, wetting agents such as condensation products of fatty alcohols with ethylene oxide, or preservatives such as alkyl p-hydroxybenzoates.

Injectable solutions or suspensions may be produced in the conventional way such as with the use of preservatives such as alkyl p-hydroxybenzoates, or stabilizers such as complexons and they are then added under sterile condition into injection vials or ampoules. The solution may also contain stabilizers and/or buffers.

The suppositories may be produced, for example, by mixing the active ingredient or active ingredient combinations with conventional carriers such as neutral fats or polyethyleneglycol or derivatives thereof. Gelatin capsules for rectal administration containing the active substance in admixture with plant oil or paraffin oil may be produced as well.

The novel method of the invention for relieving pain and/or reducing blood pressure in warm-blooded animals comprises administering to warm-blooded animals an effective amount of at least one compound of formula I or it non-toxic, pharmaceutically acceptable acid addition salts. The compounds may be administered parenterally or enterally. The usual daily dose is 1 to 30 mg/kg depending upon the method of administration and the specific compound.

In the following examples there are described several preferred embodiments to illustrate the invention. However, it should be understood that the invention is not intended to be limited to the specific embodiments.

EXAMPLE 1

2-[N-(thienyl-(2)-methyl)-N-(2,6-dichlorophenyl)-amino]-2-imidazoline

A mixture of 6.9 g (0.03 moles) of 2-(2,6-dichlorophenylamino)-2-imidazoline, 4.4 g (10% excess) of 2-chloromethylthiophene, 7 ml of triethylamine and 60 cc of anhydrous toluene was refluxed with stirring for 3 hours and after cooling, the mixture was vacuum filtered. The recovered precipitate was dissolved in dilute hydrochloric acid and the resulting solution was extracted several times with ether. The aqueous phase was adjusted to different pH values with dilute sodium hydroxide solution and was extracted at each with ether. The ether fractions with a uniform thin layer chromatography were combined, dried over drierite and evaporated under reduced pressure to dryness to obtain 2.7 g (27.6%) of 2-[N-(thienyl-(2)-methyl)-N-(2,6-dichlorophenyl)-amino]-2-imidazoline melting at 111° to 114°C. The product was soluble in organic solvents and insoluble in water.

EXAMPLE 2

1-(thienyl-(3)-methyl)-2-(2,6-dichlorophenylamino)-2-imidazoline hydrobromide 1.3 g (0.03 moles) of a 55% sodium hydride dispersion were added at 10 to 20°C to a solution of 6.9 g (0.3 moles) of 2-(2,6-dichlorophenylamino)-2-imidazoline in 50 ml of absolute tetrahydrofuran and the mixture was stirred for 2 hours at room temperature. A mixture of 5.8 g (110%) of 3-bromomethyl-thiophene and 10 ml of absolute tetrahydrofuran was added dropwise while stirring and the mixture was allowed to react at room temperature. The mixture was then refluxed for 3 hours and was then evaporated to dryness under reduced pressure. The residue was admixed with dilute hydrobromic acid and the resulting precipitate was recovered by vacuum filtration, was washed with water and dried. The product was crystallized from absolute methanol to obtain 6.0 g (49.1% yield) of 1-(thienyl-(3)-methyl)-2-(2,6-dichlorophenylamino)-2-imidazoline hydrobromide melting at 272° to 275°C. Thin layer chromatography showed the compound to be pure and the product was soluble in dimethylsulfoxide, slightly soluble in ethanol and insoluble in water.

EXAMPLE 3

Using the procedure of Example 1, a 29.4% yield of 2-[N-(thienyl-(2)-methyl)-N-(2-chloro-6-methyl-phenyl)-amino]-2-imidazoline with a melting point of 88°-90°C was obtained.

EXAMPLE 4

Using the procedure of Example 1, a 30.0% yield of 2-[N-(thienyl-(2)-methyl)-N-(2-chloro-4-methyl-phenyl)-amino]-2-imidazoline with a melting point of 106°-108°C was obtained.

EXAMPLE 5

Using the procedure of Example 1, a 29.4% yield of 2-[N-(thienyl-(2)-methyl)-N-(2-methyl-5-fluoro-phenyl)-amino]-2-imidazoline with a melting point of 88°-91°C was obtained.

EXAMPLE 6

Using the procedure of Example 1, a 27.0% yield of 2-[N-(thienyl-(3)-methyl)-N-(2,6-dichlorophenyl)-amino]-2-imidazoline with a melting point of 252°-254°was obtained.

EXAMPLE 7

Using the procedure of Example 1, a 26.8% yield of 2-[N-(thienyl-(2)-methyl)-N-(4-methoxyphenyl)-amino]-2-imidazoline with a melting point of 78°C was obtained.

EXAMPLE 8

Using the procedure of Example 1, a 22.8% yield of 2-[N-(thienyl-(2)-methyl)-N-(2,6-dichloro-4-bromophenyl)-amino]-2-imidazoline with a melting point of 172°-174°C was obtained.

EXAMPLE 9

Using the procedure of Example 1, a 39.0% yield of -[N-(thienyl-(2)-methyl)-N-(2-trifluoromethylphenyl)-amino]-2-imidazoline with a melting point of 134°-136°C was obtained.

EXAMPLE 10

Using the procedure of Example 1, a 31.1% yield of 2-[N-(thienyl-(2)-methyl)-N-(2,6-diethylphenyl)-amino]-2-imidazoline in the form of an oil was obtained.

EXAMPLE 11

Using the procedure of Example 1, a 29.2% yield of 2-[N-(thienyl-(3)-methyl)-N-(phenyl)-amino]-2-imidazoline with a melting point of 81°-83°C was obtained.

EXAMPLE 12

Using the procedure of Example 1, a 26.3% yield of 2-[N-(thienyl-(3)-methyl)-N-(2-chloro-3-methyl-phenyl)-amino]-2-imidazoline with a melting point of 222°-225°C was obtained.

EXAMPLE 13

Using the procedure of Example 1, a 21.1% yield of 2-[N-(3-methylthienyl-(2)-methyl)-N-(2,6-dichlorophenyl)-amino]-2-imidazoline with a melting point of 132°-135°C was obtained.

EXAMPLE 14

Using the procedure of Example 1, a 15.6% yield of 2-[N-(3-methylthienyl-(2)-methyl)-N-(2-chloro-3-methylphenyl)-amino]-2-imidazoline with a melting point of 104°-105°C was obtained.

EXAMPLE 15

Using the procedure of Example 1, a 31.9% yield of 2-[N-(thienyl-(2)-methyl)-N-(2,4-difluorophenyl)-amino]-2-imidazoline in the form of an oil was obtained.

EXAMPLE 16

Using the procedure of Example 2, a 38.6% yield of 1-(thienyl-(2)-methyl)-2-(2,6-dichlorophenylamino)-2-imidazoline melting at 286°-288°C was obtained.

EXAMPLE 17

Using the procedure of Example 2, a 9.7% yield of 1-(3-methylthienyl-(2)-methyl)-2-(2,6-dichlorophenylamino)-2-imidazoline melting at 273°-276°C was obtained.

EXAMPLE A

Tablets weighing 445 mg were prepared by intimately admixing 30 mg of 2-[N-thienyl-(2)-methyl)-N-(2,6-dichlorophenyl)-amino]-2-imidazoline, 160 mg of corn starch, 250 mg of secondary calcium phosphate and 5 mg of magnesium stearate and the mixture was granulated and pressed into tablets containing 30 mg of the active compound.

EXAMPLE B

Gelatin Capsules weighing 200 mg were prepared by well mixing of 25 mg of 1-(thienyl-(3)-methyl)-2-(2,6-dichlorophenylamino)-2-imidazoline hydrobromide and 175 mg of corn starch and filling the capsules.

EXAMPLE C 1.5 parts by weight of 2-[N-(thienyl-(2)-methyl)-N-(2,6-dichlorophenyl)-amino]-2-imidazoline and 0.2 parts by weight of the sodium salt of the ethylenediaminetetraacetic acid were dissolved in sufficient water and water was added to obtain a final volume of 100.0 parts by weight. The solution was filtered free of suspended particles and filled into 2 ccm ampoules under aseptic conditions. Then, the ampoules were sterilized and sealed and each ampoule contained 20 ml of the active ingredient.

Various modifications of the products and processes of the invention may be made without departing from the spirit or scope thereof and it is to be understood that the invention is to be limited only as defined in the appended claims.

We claim:

1. A compound of the formula

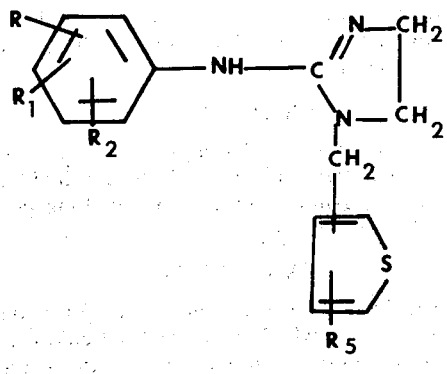

wherein

R, $R_1$ and $R_2$ are each hydrogen, fluorine, chlorine, bromine, methyl, ethyl, methoxy, trifluoromethyl or cyano, and $R_5$ is hydrogen, methyl or ethyl, or a non-toxic, pharmaceutically acceptable acid addition salt thereof.

2. A compound of claim 1 which is of the formula

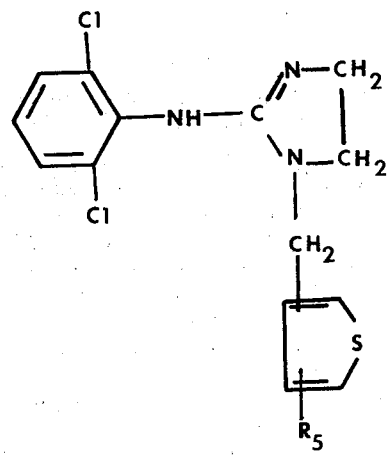

wherein $R_5$ is hydrogen or methyl, or a non-toxic, pharmaceutically acceptable acid addition salt thereof.

3. A compound of claim 2 selected from the group cosisting of 1-(thienyl-(3)-methyl)-2-(2,6-dichlorophenylamino)-2-imidazoline and its non-toxic, pharmaceutically acceptable acid addition salts.

4. A compound of claim 2 selected from the group consisting of 1-(thienyl-(2)-methyl)-2-(2,6-dichlorophenylamino)-2-imidazoline and its non-toxic, pharmaceutically acceptable acid addition salts.

5. A compound of claim 2 selected from the group consisting of 1-(3-methylthienyl-(2)-methyl)-2-(2,6-dichlorophenylamino)-2-imidazoline and its non-toxic, pharmaceutically acceptable acid addition salts.

* * * * *